United States Patent [19]
Han et al.

[11] Patent Number: 5,834,427
[45] Date of Patent: Nov. 10, 1998

[54] CASEIN PHOSPHOPEPTIDE, CASEIN CONTAINING SAME AND PROCESS FOR THE PREPARATION THEREOF

[75] Inventors: Sang Kee Han, 123-1201, Kwanakhyundai Apt., 1, Bongchun-dong, Kwanak-ku, Seoul; Yoo Cheol Shin, Seoul, both of Rep. of Korea

[73] Assignee: Sang Kee Han, Seoul, Rep. of Korea

[21] Appl. No.: 621,564

[22] Filed: Mar. 25, 1996

[30] Foreign Application Priority Data

Mar. 23, 1995 [KR] Rep. of Korea .................... 1995 6259

[51] Int. Cl.⁶ .......................... A61K 38/17; C07K 14/47; A23T 3/10
[52] U.S. Cl. .................................. 514/12; 514/2; 514/775; 514/902; 530/324; 530/360; 530/416; 530/417; 530/420; 530/419; 530/427; 426/539
[58] Field of Search ..................................... 530/324, 419, 530/420, 416, 427, 360, 417; 514/775, 12, 21, 902; 426/580

[56] References Cited

U.S. PATENT DOCUMENTS

| | | | |
|---|---|---|---|
| 5,085,871 | 2/1992 | Horikawa et al. | 426/2 |
| 5,227,154 | 7/1993 | Reynolds | 424/49 |
| 5,405,756 | 4/1995 | Naito et al. | 435/68.1 |

FOREIGN PATENT DOCUMENTS 90406  5/1983  European Pat. Off. .

OTHER PUBLICATIONS

Patent Abstracts of Japan, vol. 18, No. 71 (C–1162), 1994, JP 4–88459 (Meiji Seika Kaisha Ltd.).
Dialog Abstract, Biosis No.:99229799. Stevenson et al. 1996. J. of Agricultural and Food Chemistry 44(9):2825–2828, 1996.

*Primary Examiner*—Robert A. Wax
*Assistant Examiner*—Gabriele E. Bugaisky
*Attorney, Agent, or Firm*—Lowe, Price, LeBlanc & Becker

[57] ABSTRACT

The present invention relates to a purified casein phosphopeptide(CPP) having a novel amino acid sequence and a purified casein including same wherein the 25th Arg from N-terminal in a conventional CPP is replaced by Cys, rendering the CPPs to forming a dimer by disulfide bond. In the corresponding DNA sequence, cytosine is replaced by thymine to cause the amino acid replacement from Arginine (Arg) to Cysteine(Cys). The CPP or the casein containing same has an improved ability of solubilizing minerals and absorbing thereof in animals. The CPP or the beta-casein H containing same can be added to foodstuffs, beverages, medication, cosmetics, feed in an effective amount of enhancing a mineral absorption in animals. An oral composition comprising the beta-casein H or the inventive CPP and a pharmaceutically acceptable carrier can reduce or relieve a dentinal hypersensitivity.

15 Claims, 3 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:1:

```
Arg Glu Leu Glu Glu Leu Asn Val Pro Gly Glu Ile Val Glu Ser Leu
 1               5                  10                  15
Ser Ser Ser Glu Glu Ser Ile Thr Cys Ile Asn Lys
            20                  25
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:2:

```
Arg Glu Leu Glu Glu Leu Asn Val Pro Gly Glu Ile Val Glu Ser Leu
 1               5                  10                  15
Ser Ser Ser Glu Glu Ser Ile Thr Arg
            20                  25
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: DNA (other nucleic acid)

( x i ) SEQUENCE DESCRIPTION: SEQ ID NO:3:

```
CAACAGCCTT ATTCAGAAGA GTGG                                           24
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear     ( i i ) MOLECULE TYPE: DNA (other nucleic acid)

( x i ) SEQUENCE DESCRIPTION: SEQ ID NO:4:

```
CAGTGGGATG ACAGAAAGTA GTCGTATAGG                                     30
```

( 2 ) INFORMATION FOR SEQ ID NO:5:

( i ) SEQUENCE CHARACTERISTICS:
        ( A ) LENGTH: 194 base pairs (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 43..67

(ix) FEATURE:
        (A) NAME/KEY: CDS
        (B) LOCATION: 159..194

(xi) SEQUENCE DESCRIPTION: SEQ ID NO:5:

```
TTTTTAAAG CTAGACCTGA TTTTATTTTT ATTTTTCCAA AG GAA TCT ATT ACA           54
                                               Glu Ser Ile Thr
                                                1

TGC ATC AAT AAG G TAAAACCCCT CATATTTAAA TGTACATTTT TTTAAATTTC          107
Cys Ile Asn Lys
 5

ATGTTTGATT TTTATAAACA GCATTTATTT ATGTATTTTT TTTTAACCA G AAA ATT        164
                                                       Lys Ile
                                                        1

GAG AAG TTT CAG AGT GAG GAA CAG CAG CAA                                194
Glu Lys Phe Gln Ser Glu Glu Gln Gln Gln
         5                   10
```

(2) INFORMATION FOR SEQ ID NO:6:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:6:

```
Glu Ser Ile Thr Cys Ile Asn Lys
 1               5
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:7:

```
Lys Ile Glu Lys Phe Gln Ser Glu Glu Gln Gln Gln
 1               5                   10
```

CASEIN PHOSPHOPEPTIDE, CASEIN CONTAINING SAME AND PROCESS FOR THE PREPARATION THEREOF

FIELD OF THE INVENTION

The present invention is generally directed to a casein phosphopeptide having a novel amino acid sequence, a beta-casein H containing same and process for the preparation thereof. In particular, the present invention relates to a casein phosphopeptide having a novel amino acid sequence which solubilizes minerals to promote an absorption thereof in the alimentary tract in animals.

DESCRIPTION OF THE PRIOR ART

An obesity is one of the most dangerous hazard to threaten the health of modern people, which is largely due to high calory foods and beverages insufficient in vitamins and minerals. It is known that such unbalanced foodstuffs are responsible for diseases of adult people such as an osteoporosis.

In order to prepare balanced foodstuffs, many researchers have tried to add one or more insufficient minerals to the foodstuffs. However, almost those attempts have been found unsuccessful because an addition of one mineral results in an absorption inhibition or decrease of other minerals in animals. Accordingly, it is desired to increase a mineral absorption rate in animals without adding minerals to foodstuffs.

In general, minerals should be kept in a soluble state to be absorbed into animals. However, as contents moves through the small intestine in animals, a pH thereof shifts from a neutral to an alkaline state. In accordance with the change of pH in the small intestine, a large portion of minerals becomes insoluble to cause a precipitation. Concerning a calcium absorption, as a calcium moves through the small intestine, a portion of soluble calcium decreases in inverse proportion to an increase of pH therein.

A casein is one kind of protein contained in bovine or human milk, and α, β and γ types have been reported. In particular, β-casein have $A^1, A^2, A^3$, B, C, D and E variants whose primary structures have been already suggested(W. N. Eigel, et al, Nomenclature of Proteins of Cow's milk (5th Revision), J. Dairy Sci. Vol. 67, No. 8, pp. 1607–8 (1984)).

Further, a casein phosphopeptide (hereinafter, referred to as "CPP") is contained in a casein which is abundant in milk. Up to date, CPP has been recognized an important material which may increase a mineral absorption rate in animals.

Since CPP or a casein including same has a potent ability to solubilize minerals such as calcium and iron in an aqueous solution, many attempts have been made to prepare balanced foods or beverages by use of CPP, in order to treat or relieve a mineral malnutrition in animals.

Irrespective of $A^1, A^2, A^3$, B, C, D and E variants of β casein, their structure and amino acid sequence of CPP produced therefrom remain same, the sequence of which is shown as follows: (SEQ. ID NO: 2)

As illustrated above, a conventional CPP has 25 amino acids; and three successive phosphoserines and two glutamic acid residues coming thereafter form a strong negative charge area, thereby providing an active site with respect to a calcium (Naito, "The Mechanism of Enhancement in Intestinal Calcium Absorption with Phosphopeptides Derived during Casein Digestion," J. of Japanese Nutr. and Food, Vol. 39, No. 6, pp. 433–439, (1986)). Naito have suggested that CPP enhance an Fe absorption as well as a Ca absorption in the small intestine in animals.

It is known that when a casein containing CPP is supplied into animals together with calcium, a soluble calcium significantly increases in the small intestine in animals compared with a supply of calcium alone. While an active transport prevails in the upper small intestinal tract in the calcium absorption, a passive transport is dominant in the lower small intestinal tract based on a concentration equilibrium. It is also suggested that vitamin D and lactose further promote the calcium absorption in animals. Although an absorption rate of calcium reveals high in the upper part of the small intestine, i. e., the duodena in animals, the retention time of contents is so short that the whole amount of calcium absorption therein is relatively low. In contrast, due to the long retention time of a diet, the ileum located in the lower part of the small intestine is an important part at which a large portion of calcium is absorbed. In fact, 62 or 88% of calcium is absorbed in the ileum in rats; and the calcium absorption in a human body excised with the ileum decreases greatly. It is accordingly understood that CPP plays an important role in calcium absorption (Sato et al., "Casein phosphopeptide contributing to an absorption of Ca in dairy product," Chemistry and Biology, Vol. 23, No. 7, p. 418 (1985)).

Sato et al. have further reported that a series of experiments was carried out in order to ascertain a role of phosphate residues in casein. In the experiments, four groups of rats ware fed with foods containing a phosphorylated casein, a dephosphorylated casein, a gluten and a gelatine, respectively. As the results, the group fed with a phosphorylated casein showed the largest amount of soluble calcium and the highest value in the calcium absorption rate in the small intestine in the animals. Also, CPP can be produced from bovine milk by tryptic digestion (Sato et al., "The Necessity for the Phosphate Portion of Casein Molecules to Enhance Ca Absorption from the Small Intestine," Agric. Biol. Chem. Vol. 47, No. 10, pp. 2415-7 (1983)).

In order to extract a casein from milk, Gordon described a method including: removing fat from milk, adding a hydrochloric acid to the resultant to reach 4.6 of pH, centrifugating the precipitated casein, and subjecting the resultant to a dehydration and a freeze-drying (W. G. Gordon et al., Fundamentals of Diary Chemistry, 2th ed., AVI Publishing Co. (1974)). Also, Spellacy proposed a method to precipitate a casein from milk by adding a lactic acid produced from Streptococcus lactis (J. R. Spellacy, Casein, Dried and Condensed Whey, Lithotype Process Co. (1953)). Fox taught a technic of adding a rennet to precipitate a casein from milk (K. K. Fox, Byproducts from Milk, 2th ed., AVI Publishing Co. (1970)).

```
Arg—Glu—Leu—Glu—Glu—Leu—Asn—Val—Pro—Gly—Glu—Ile—Val—Glu—Ser(P)—
1                   5                      10                      15

Leu—Ser(P)—Ser(P)—Ser(P)—Glu—Glu—Ser—Ile—Thr—Arg
16                         20                        25
``` wherein Ser(P) represents a phosphorylated serine.

From a casein obtained as above, various methods for producing a conventional CPP have been reported. Peterson taught a process comprising: subjecting a casein to a tryptic hydrolysis, controlling pH of the hydrolyzate to 4.7, removing unreacted casein, adding $BaCl_2$ and ethanol to the supernant of the hydrolyzate and recovering CPP (R. F. Peterson et al., J. Amer. Chem. Soc., Vol. 80, p. 95 (1958)).

Naito showed a process for producing CPP comprising: digesting a casein by digestive enzyme, isolating a coarse CPP by gel-filtration of Sephadex G-25 and purifying CPP by passing the coarse mixture through an ion-exchange resin(Naito et al., Agric. Biol. Chem., Vol. 38, p. 1543. (1974)).

Also, U.S. Pat. No. 4,361,587 discloses a method for producing phosphopeptides comprising: subjecting a casein to an enzymatic hydrolysis, recovering the resulting hydrolyzate, subjecting said hydrolyzate to a first membrane ultrafilteration, recovering the retentate, disaggregating the phosphopeptides contained therein, subjecting the retentate containing disaggregated phosphopeptide to a second membrane ultrafilteration.

Japanese Patent Publication No. Sho 59-159793 discloses a process for producing CPP comprising: subjecting a casein to a trypsin hydrolysis to produce CPP, adding a bivalent ferric ion to the resultant hydrolyzate to precipitate and recovering CPP.

Furthermore, Korean Laid-open Patent Publication No. 93-10190 illustrates a use of proteolytic enzyme obtained from Streptococcus faccalis var. liquefaciens.

A casein or CPP have been widely used in various purposes. By using its mineral solubilizing effect, Japanese Laid-open Patent Publication No. Hei 5-336894 discloses health foodstuffs enriched with CPP. Japanese Laid-open Patent Publication No. Hei 5-176712 also teaches foodstuffs containing CPP and alkaline phosphatase. Further, Japanese Laid-open Patent Publication No. Hei 4-299942 illustrates an improved feed for the fowls containing CPP.

Both PCT publication No. WO 94/00146 and U.S. Pat. No. 5,015,628 have suggested an oral composition comprising CPP to prevent or relieve dental calculuses or a dental hypersensitivity. In addition, Japanese Laid-open Patent No. Hei 1-269499 teaches a process for producing a skin or a hair care products containing CPP.

The disclosure of all references cited herein is incorporated by reference.

SUMMARY OF THE INVENTION

The present inventors have endeavored to enhance the intestinal mineral absorption in connection with CPP and finally found a novel CPP which differs its structure and the amino acid sequence from those of a conventional CPP.

The inventive purified CPP of a novel amino acid sequence referred herein as SEQ. ID NO: 1 having 28 amino acids, wherein the 25th Arg from N-terminal in the conventional CPP is substituted by Cys. In the corresponding DNA sequence, cytosine is replaced by thymine to cause the amino acid replacement from Arginine(Arg) to Cysteine (Cys).

Another aspect of this invention, there is provided a new purified casein including the instant CPP which was named as "beta-casein H" by the present inventors.

It is therefore an object of the invention to provide a novel CPP having an amino acid sequence of SEQ. ID NO: 1.

Another object of the invention is to provide a novel beta-casein H containing the inventive CPP having the amino acid sequence of SEQ. ID NO: 1.

Still another object of the invention to provide the respective processes for producing the inventive CPP and the beta-casein.

Still further object of the invention is to provide compositions for various useful purposes comprising the inventive CPP or the beta-casein H.

BRIEF DESCRIPTION OF DRAWINGS

Other objects, features and advantages of the invention will become apparent from the following description of the preferred embodiment taken in conjunction with the accompanying drawings in which.

DETAILED DESCRIPTION FOR THE PREFERRED EMBODIMENT

Proteins and minerals generally tend to be bound to each other, and the types and strength of such couplings are largely dependent upon their higher structures i.e., secondary or tertiary structure (Naito, "The Mechanism of Enhancement in Intestinal Calcium Absorption with Phosphopeptides Derived during Casein Digestion," J. of Japanese Nutr. and Food, Vol. 39, No. 6, pp. 433, 436, (1986)). Due to differences of the amino acid sequence and primary structure, the inventive CPP and the beta-casein H containing same show an improved ability to solubilize minerals including calcium in the small intestine; and, therefore, it naturally entails an enhancement of mineral absorption in animals.

In accordance with the present invention, there is provided a novel purified CPP having a novel amino acid sequence of SEQ. ID NO: 1. In the present sequence, the 25th Arg of a conventional CPP is replaced by Cys. In addition, the novel CPP has three amino acids of isoleucine (Ile), asparagine(Asn) and lysine(Lys) after the 25th cysteine; and, therefore, the inventive CPP has 28 amino acids. Due to Cys, the new CPPs tend to form a dimer each other by a disulfide bond.

As already suggested, three successive phosphoserines (17th to 19th) and two glutamic acid residues (20th and 21st) form a strong negative charge area, which provide an active site with respect to a calcium (Naito, supra). It is understood that a dimer of the novel CPPs protects a stability of the above-mentioned active area of three phosphoserines and two glutamic acids; and, therefore, the the inventive CPP has an improved ability to solubilize minerals.

While the present CPP has 28 amino acid residues, it is susceptible to a proteolytic hydrolysis, especially between the 3rd Leu and the 4th Glu, and between the 6th Leu and the 7th Asn from the N-terminal. Accordingly, two kinds of fragments may be produced in the small intestine in animals, i.e., one has 25 residues removed of Arg-Glu-Leu, and the other has 22 residues removed of Arg-Glu-Leu-Glu-Glu-Leu residues from the N-terminal. However, any kind of fragments produced by a hydrolysis has a CPP function of sulubilizing minerals in the small intestine as long as they have the active site (17th to 21st residues). Accordingly, it is appreciated that any fragments containing the active site (17th to 21st residues) and the 25th Cys in the peptide sequence of SEQ. ID NO: 1 should fall within the scope of the present invention.

In the present invention, there is provided the purified beta-casein H containing the inventive CPP which has an active site to minerals; and, therefore, the beta-casein H also solubilizes minerals in the small intestine in animals.

It should be noted that the inventive CPP or the beta-casein H may be used as such, or in the form of their alkali metal, alkaline earth metal or transition metal salts. Typical examples are a sodium, calcium, calcium phosphate, calcium fluoride phosphate, ferric, zinc, potassium and magnesium salt.

In another aspect of the invention, there is provided a process for producing a beta-casein H containing the CPP having the amino acid sequence of SEQ. ID NO: 1 comprising the steps of: selecting milk containing the beta-casein H, adding an acid or a rennet to the milk to precipitate, and recovering the precipitated beta-casein H.

Figure 1:
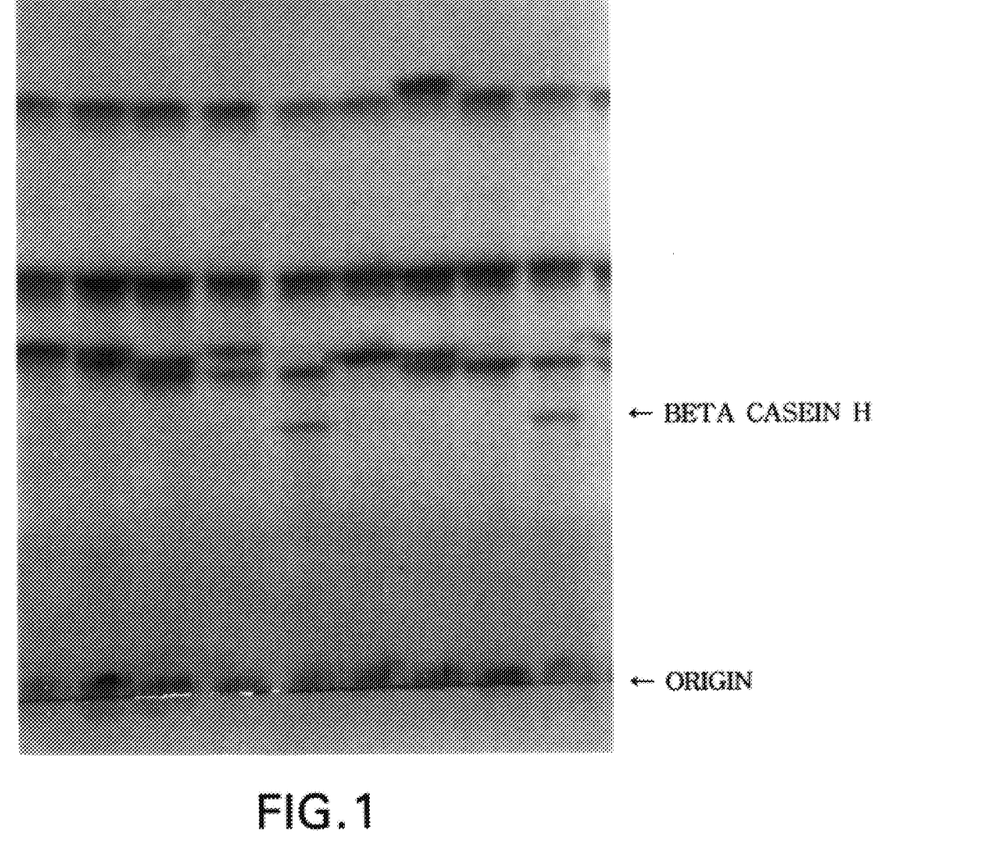
FIG. 1 is a photograph of electrophoresis with respect to the beta-casein H in accordance with the present invention.

In the process, the selection of milk containing a beta-casein H is carried out by an electrophoresis which shows a characteristic band in FIG. 1. Representative examples of acids which can preferably be added to milk include: a hydrochloric acid and lactic acid. The precipitated beta-casein H can be recovered by chromatographys. It is preferred that an anion exchange chromatography and then a cation exchange chromatography are conducted successively.

In still another aspect of the present invention, there is provided a method for producing a casein phosphopeptide having an amino acid sequence of SEQ. ID NO: 1 comprising the steps of: selecting a beta-casein H, subjecting the beta-casein H to a hydrolysis by adding one or more proteases thereto, adding one or more inorganic ions to the hydrolyzate to precipitate a peptide, and recovering the precipitated casein phosphopeptide.

The beta-casein H can be identified by the peculiar band as shown in FIG. 1 as a result of an electrophoresis.

In the above process, various kinds of proteases may be used, typical examples of which includes a trypsin, pancreatin, chymotrypsin, pepsin, papain, pronase and thermolysin. The protease is preferably mixed in an amount ranging from 0.001% to 2% by weight based on the casein.

The inorganic ion is selected from the group consisting of Fe, Ca, Ba, Cu, Zn, Mn and Co. Among them, a ferric ion is preferred for which $FeCl_3$ is used as a source. As a concentration of inorganic ion becomes higher, an amount of the precipitate increases; however, the purity of CPP may be deteriorated. Accordingly, the preferable concentration of inorganic ion ranges from 5 to 50 mM. When an ethanol is added together with the inorganic ion, the precipitation of CPP proceeds effectively.

Instead of adding inorganic ions, the hydrolyzate may be subjected to a chromatography such as HPLC or gel filtration chromatography.

In addition, the CPP in accordance with the instant invention may be produced through a chemical synthesis referring to its amino acid sequence of SEQ. ID NO: 1. Further, a microorganism containing the genetic information of SEQ. ID NO: 1 may be made by a conventional transformation method to produce the creative CPP. Furthermore, a transgenic animal may be produced by introducing a genetic information of the SEQ. ID NO: 1 into an animal other than a cattle, such as sheep and goat.

Since the subject CPP or the beta-casein H is produced from milk containing the beta-casein H, it is necessary to produce milk containing the beta-casein H in a large scale. For this purpose, there is provided a process for producing milk containing a beta-casein E-I comprising the steps of: selecting a bovine individual which produces milk containing the beta-casein H, hybridizing said bovine with another bovine breed which secretes a lot of milk to obtain F1 descendants, selecting a cow which produces milk containing the beta-casein H among said F1 descendants, and extracting milk containing the beta-casein H from said cow.

In order to select a bovine individual of the beta-casein H, a material containing DNA extracted from a cattle such as blood, tissue and semen is analyzed for a DNA sequence to compare with the sequence of SEQ. ID NO: 1. referred herein. As an alternative, an electrophoresis may conducted for milk to find a unique band as shown in FIG. 1. The selected bovine individual of the beta casein H is then copulated with another bovine species which produces much milk, for example, Holstein species. It has been found that some descendants (F1) obtained therefrom have a genetic information of the beta-casein H which produce milk containing the desired beta-casein H. Thus selected improved bovine individual produces milk containing the beta-casein H with a high productivity, which is most suitable for the mass production of the beta-casein H in accordance with the present invention Accordingly, the present invention provides a composition for health food or beverage comprising the purified CPP or the purified beta-casein H and edible carriers. The composition may further comprise vitamin D and lactose to promote a mineral absorption. The composition may preferably comprise minerals such as ion and calcium to supply minerals to animals. Examples of the composition include: milk, powdered milk for baby or patients, yoghurts (liquid, creamy or frozen type), cheese, weaning diet, confectionery, breads, ice creams, bean curds, candy, frozen sweets, oil-and-honey pastry, chocolate, caramel, natural or artificial juices, boiled fish pastes, thirsty quenchers (isotonic sports drinks), powdered tea, mayonnaise, dressings and the like.

Particularly, the CPP or the beta-casein H in accordance with the present invention is preferably added to foodstuffs excluding lactose for infants or adults who are allergic thereto.

Still another aspect of this invention, there is provided a medical composition comprising a purified beta-casein H or a purified CPP having an amino acid sequence of SEQ. ID NO: 1 in an effective amount of preventing, treating or relieving a disease caused by a mineral malnutrition in animals, and a pharmaceutically acceptable carrier. The disease caused by a mineral malnutrition such as osteoporosis or anemia can be treated or relieved by orally administering the medical composition above. The CPP or the beta-casein H in the medical composition may be administered in an amount of 0.1 g to 100 g per day. The composition may preferably comprise minerals such as iron or calcium.

The present invention further provides an oral composition comprising the inventive purified CPP or the purified beta-casein H and a pharmaceutically acceptable carrier. The oral composition include: aqueous, aqueous-alcohol or alcohol solution or dispersion of casein or the CPP in the form of a mouthwash, dentifrice, toothpaste, toothpowder, gel, lozenge, tablet, chewing gum, or any other suitable form of oral composition. The pH of the preparations preferably ranges from 2 to 10. The preferred oral composition may also contain an effective amount of phosphatase inhibitor or phosphopeptide stabilizing agent such as carrageenan and anionic polymer.

The inventive CPP or casein containing same may be added to a composition i.e., skin or hair care products, or a feed composition in an effective amount of enhancing a mineral absorption in animals, and edible carriers.

Due to a competent ability of solubilizing minerals in animals, the present compositions including the instant CPP or the beta-casein H show an improved effects over the prior compositions including the conventional CPP or the casein.

Since the CPP or the beta-casein H has a higher mineral solubilizing effect, it is of course used for every purposes noted above, rendering products including same more effective.

The following Examples are given for the purpose of illustration only and are not intended to limit the scope of the invention.

EXAMPLE 1
Preparation of purified beta-casein H in accordance with the present invention Bovine milk was centrifugated at 5,000 RPM for 20 minutes, followed by removing the supernant fatty layer. The resultant was added to starch gel (Connought Medical Research Lab.); and an electrophoresis was carried out at 150 volts for 12 hours by using a buffer (pH: 1.5) consisting of: 850 ml of deionized water, 100 ml of acetic acid and 50 ml of formic acid. The gel was stained by 10% of nigrosin solution for 30 minutes and then destained by adding 50% of methanol for 5 hours. The resulting electrophoresis photograph is shown in FIG. 1, wherein the beta-casein H is identified by its specific band.

Figures 2A, 2B, 2C:
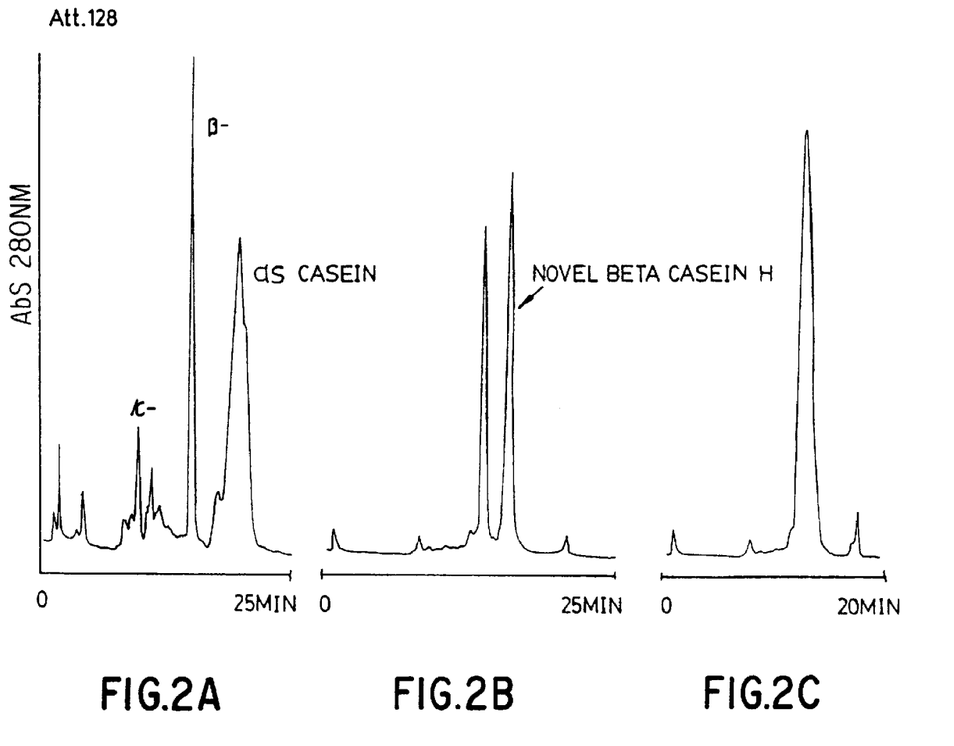
FIG. 2(a) is a chromatogram showing the beta-casein peak after passing the casein through a anion exchange column.
FIG. 2(b) is a chromatogram showing the specific beta-casein H peak after passing the beta-casein of FIG. 2(a) through a first cation exchange column.
FIG. 2(c) is a chromatogram showing the specific beta-casein peak after passing the beta-casein H of FIG. 2(b) through a second cation exchange column.

Bovine milk which was found to contain the beta-casein H as above was then centrifugated, followed by removing fatty layer of the supernant. The casein protein was precipitated by adding a hydrochloric acid, and subjected to a free-drying. By passing 10 g of the casein through an anion exchange column (Model: Mono Q 5/5 manufactured by Pharmarcia Co.) using 20 mM of imidazole-HCl buffer (pH 7.0), a purified beta-casein was obtained. The chromatogram is shown in FIG. 2(a).

The resulting beta-casein was subjected to a first cation exchange column (Model: Mono S 5/5 manufactured by Pharmarcia Co.) by using 50 mM of sodium acetate buffer (pH 5.0) to give the beta-casein H. The result is shown in FIG. 2(b). A second cation exchange column was carried out for the casein to yield 1.5 g of the beta-casein H in a pure form. The chromatogram is shown in FIG. 2(c).

EXAMPLE 2
Preparation of the inventive purified CPP by trypsin hydrolysis

Figure 3:
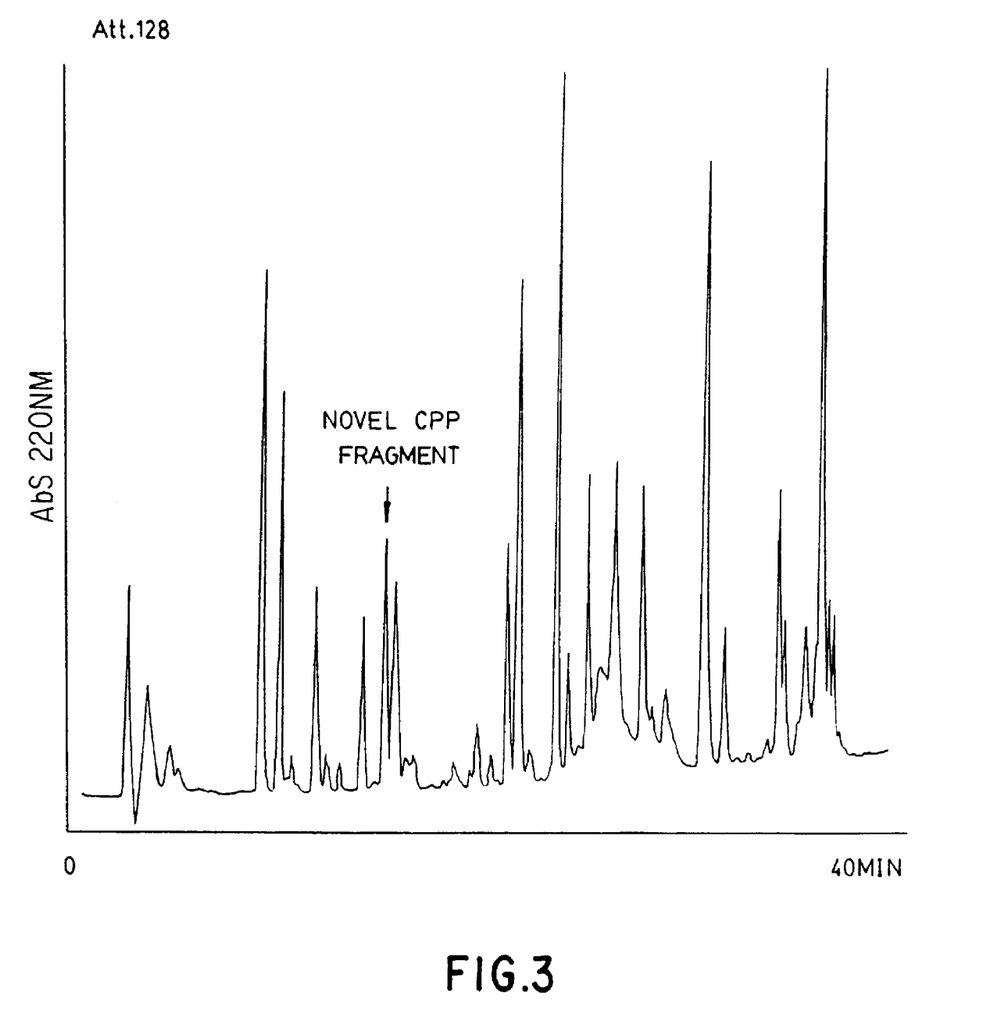
FIG. 3 is an HPLC chromatogram showing the specific peak of CPP in accordance with the present invention.

To the beta-casein H obtained in Example 1, 0.01 wt % of trypsin (manufactured by Sigma Co.) was added. The mixture was dissolved in phosphate buffer to hydrolyze at a temperature of 37° C. for 12 hours. After the completion of the reaction, the hydrolyzate was heated to 90° C. for 30 minutes to deactivate enzymes therein. The pH of the mixture was controlled to 4.6 and then the unreacted precipitate was removed. The hydrolyzate was subjected to HPLC (RP-column manufactured by Merk) with an acetonitrile buffer to yield a pure CPP (purity: 99%). The chromatogram is illustrated in FIG. 3, which describes a specific peak of the beta-casein H in accordance with the present invention.

The purified CPP was lyophilized and then subjected to a protein sequencer (Applied-Bio System Co.) to provide the amino acid sequence of SEQ. ID NO: 1

EXAMPLE 3
Preparation of the inventive purified CPP by adding ferric ion 10 g of the beta-casein H obtained in accordance with the same process as in Example 1 and 0.1 g of trypsin were dissolved in 100 ml of phosphate to hydrolyze at 37° C. for 12 hours. To the resulting solution, $FeCl_3$ was added to reach 20 mM of $Fe^{++}$ concentration of the solution and 50% (v/v) of ethanol was added thereto to precipitate a peptide. Thus precipitated peptide was lyophilized and then subjected to a gel filtration chromatography to give 1.2 g of the CPP (purity: 90%).

EXAMPLE 4
DNA analysis for the purified beta-casein H 20 ml of blood was extracted from a Korean Native Cattle and then a DNA was purified according to a conventional method proposed by Sambrook (Sambrook et al., Molecular Cloning, Cold Spring Harbor Lab. Press, (1989)).

To amplify a DNA fragment containing the substituted amino acid in the beta-casein, a primer was prepared by referring to a process suggested by Bosing (Bosing et al., Complete Nucleotide Sequence of the Bovine Beta-casein Gene, Aust, J. Biol. Sci., Vol. 41, p. 527 (1988)). The DNA sequence of the prepared primer is as follows:

Primer 5'-CAACAGCCTTATTCAGAAGAGTGG (SEQ. ID NO: 3)

3'-CAGTGGGATGACAGAAAGTAGTCGTATAGG (SEQ. ID NO: 4)

0.5 $\mu$g of the purified DNA, 0.5 $\mu$l of each primers (100 pmol/$\mu$l), 5 $\mu$l of dNTP, 5 $\mu$l of 10× buffer, 1 $\mu$l of Taq polymerase (1 unit) and 33 $\mu$l of distilled water were mixed. The DNA was denatured by heating the mixture at a temperature of 94° C. for 5 minutes. Thereafter, PCR (polymerase chain reaction) cycles were repeated 30 times for 60 seconds at 94° C., 60 seconds at 57° C. and 60 seconds at 72° C. After completing the PCR reactions, 5 minutes of extension time was provided to form double stranded helices from the amplified DNA fragments.

The amplified DNA was purified by an electrophoresis using 2% of agarose (Gibco Co.) and then the DNA sequence was analyzed by Automatic DNA sequencer (Applied Bio System Co.). The analyzed DNA sequence for the part of the CPP having the substituted amino acid residue is as follows: (SEQ. ID NO: 5)

|  | intron 4 | exon 5 |  |  |
|---|---|---|---|---|
| TTTTTTAAAGCTAGACCTGATTTTATTTTTATTTTTCCAAAG | | GAA | TCT | ATT |
| | | Glu | Ser | Ile |

|  |  |  |  | intron 5 |
|---|---|---|---|---|
| ACA | TGC | ATC | AAT | AAG | GTAAAACCCCTCATATTTAAATGTACATTTTTTAA |
| Thr | <u>Cys</u> | Ile | Asn | Lys | |

-continued
ATTTCATGTTTGATTTTTATAAACAGCATTTATTTATGTATTTTTTTTTAACCAG exon 6

| AAA | ATT | GAG | AAG | TTT | CAG | AGT | GAG | GAA | CAG | CAG | CAA |
|-----|-----|-----|-----|-----|-----|-----|-----|-----|-----|-----|-----|
| Lys | Ile | Glu | Lys | Phe | Gln | Ser | Glu | Glu | Gln | Gln | Gln |

As shown above, the 13rd base in exon 5 is replaced from cytosine to thymine evidencing the replacement of amino acid from Arg to Cys in the CPP in the present invention.

EXAMPLE 5

Mass Production of the purified beta-casein H by animal secretion

For a mass production of the beta-casein H by way of an animal secretion, a Korean Bull ($A^1H$ type) having the genetic information of the beta-casein H identified by the process as shown in Example 4 was copulated with five Holstein cows (two of $A^1A^1$, two of $A^1A^2$ and one $A^2A^2$ types) to give birth to two male calves and three female calves. The DNA analyses for the three female calves were conducted to find one female calf ($A^1H$) and one male calf ($A^2H$) of the beta-casein H as heterozygotes.

Thus obtained female calf (F1) having the genetic information of the beta-casein H ($A^1H$) was raised and conceived for 28 months from its birth date. The milk produced therefrom was found to contain the beta-casein H with an yield of approximately 4.5 Kg per day. That is, the milk productivity of the cow (F1) revealed 3 times higher than the prior Korean Cattle of the beta-casein H.

EXAMPLE 6

Efficacy test for calcium solubilizing effect In vivo

Forty Wister Rats weighing about 120 g on an average were supplied with a controlled diet consisting of 24 wt % of crude proteins, 5 wt % of crude fats, 60 wt % of starches, 5 wt % of crude fibers, 5 wt % of minerals and 1 wt % of vitamins for a week and then starved for 24 hours. The rats were divided into 4 groups, each group including 10 rats.

Rats of the first group were supplied with a controlled diet including 10 wt % of the beta-casein H for 1.5 hours.

Rats of the second group were supplied with a controlled diet including 10 wt % of a conventional beta-casein for 1.5 hours.

Rats of the third group were supplied with a controlled diet including 1 wt % of the CPP in accordance with the present invention for 1.5 hours.

Rats of the fourth group were supplied with a controlled diet including 1 wt % of the conventional CPP for 1.5 hours.

All rats were allowed to freely have the controlled diets as much as they can. One hour after the completion of the above feeding, all rats were anesthetized, and the small intestines were excised therefrom. The small intestines were washed with a saline solution and then divided into two parts, i.e, the upper part and the lower part.

Thereafter, the contents in the small intestine were isolated, homogenized and centrifugated. A calcium in the supernant was measured three times by an atomic absorption spectrometer (Perkin Elmer Co.). The results are shown in Table 1 and 2 below.

TABLE 1

Calcium concentration in the small intestine in case of casein feed

|  | 1st Group | 2nd Group | Improvement (%) |
|---|---|---|---|
| Upper part | 16.25 ± 1.8 | 15.49 ± 1.7 | 4.9 |
| Lower part | 42.23 ± 2.5 | 35.11 ± 2.3 | 20.2 |
| Total | 58.48 ± 2.2 | 50.60 ± 2.0 | 15.5 |

*mean ppm ± standard deviation

TABLE 2

Calcium concentration in the small intestine in case of CPP feed

|  | 3rd Group | 4th Group | Improvement (%) |
|---|---|---|---|
| Upper part | 17.18 ± 1.9 | 16.05 ± 1.3 | 7.0 |
| Lower part | 51.02 ± 3.1 | 39.33 ± 2.8 | 29.8 |
| Total | 68.20 ± 2.5 | 55.38 ± 2.1 | 23.1 |

*mean ppm ± standard deviation

As shown in Table 1 and 2 above, the average concentration of soluble calcium in the first group rats supplied with the beta-casein H showed 58.48 ppm, which amounts to approximately 15% improvement over that of the second group rats supplied with the prior casein.

Also, the average concentration of soluble calcium in the third group rats supplied with the present CPP revealed 68.20 ppm, which amounts to 23% improvement over that of the fourth group rats supplied with the prior CPP.

Accordingly, it appears that the inventive CPP and the beta-casein H have an unexpectedly surprising calcium solubilizing effect in vivo over the conventional casein and CPP.

While the invention has been described with reference to a preferred embodiment, it should be apparent to those skilled in the art that many changes and modifications may be made without departing from the spirit and scope of the invention as defined in the claims.

What is claimed is:

1. A purified casein phosphopeptide having an amino acid sequence of SEQ. ID NO: 1.

2. A purified beta-casein H containing a casein phosphopeptide having an amino acid sequence of SEQ. ID NO: 1.

3. A process for producing a beta-casein H containing a casein phosphopeptide having an amino acid sequence of SEQ. ID NO: 1 comprising the steps of:

selecting milk containing the beta-casein H;
   adding an acid or a rennet to the milk to precipitate; and
   recovering the precipitated beta-casein H containing a casein phosphopeptide having an amino acid sequence of SEQ. ID NO: 1.

4. The process of claim 3, wherein said step of selecting milk containing a beta-casein H is accomplished by electrophoresis.

5. The process of claim 3, wherein said step of recovering the precipitated beta-casein H is accomplished via chromatography by anion exchange, followed by cation exchange chromatography.

6. A process for producing a casein phosphopeptide having an amino acid sequence of SEQ. ID NO: 1 comprising the steps of:

obtaining a beta-casein H in accordance with the process of the claim 3;
   subjecting the beta-casein H to a hydrolysis by adding one or more proteases thereto;

adding at least one inorganic ion to the obtained hydrolyzate to precipitate a peptide; and recovering the precipitated casein phosphopeptide.

7. The process of claim 6, wherein said protease is selected from the group consisting of trypsin, pancreatin, chymotrypsin, pepsin, papain, pronase and thermolysin.

8. The process of claim 6, wherein said inorganic ion is selected from the group consisting of Fe, Ca, Ba, Cu, Zn, Mn, and Co ions.

9. The process of claim 8, wherein said inorganic ion is an Fe ion generated from $FeCl_3$.

10. The process of claim 6, further comprising the step of adding ethanol together with the inorganic ion.

11. An additive for health food or beverage comprising a purified beta-casein H or a purified casein phosphopeptide having an amino acid sequence of SEQ. ID NO: 1 in an effective amount for enhancing calcium absorption in an human, and an edible carrier.

12. The additive as recited in claim 11, further comprising calcium or iron.

13. The additive as recited in claim 11, further comprising vitamin D or lactose.

14. The additive as recited in claim 11, wherein said food or beverage is selected from the group consisting of milk, powdered milk, yoghurts, cheese, weaning diet, confectionery, breads, ice cream, bean curds, candy, frozen sweets, oil-and-honey pastry, chocolate, caramel, natural or artificial juices, boiled fish pastes, thirst quenchers, isotonic sports drinks, powdered tea, mayonnaise and dressings.

15. An oral composition for the treatment of dentinal hypersensitivity comprising a dentinal hypersensitivity reducing or relieving amount of purified beta-casein H or purified casein phosphopeptide having an amino acid sequence of SEQ. ID NO: 1 and a pharmaceutically acceptable carrier.

* * * * *